(12) United States Patent
Amano (10) Patent No.: US 11,571,385 B2
(45) Date of Patent: Feb. 7, 2023

(54) SELF-EMULSIFIABLE COMPOSITION, PRODUCTION METHOD THEREFOR, NANOEMULSION, AND PRODUCTION METHOD THEREFOR

(71) Applicant: Kewpie Corporation, Tokyo (JP)

(72) Inventor: Yohei Amano, Chofu (JP)

(73) Assignee: Kewpie Corporation, Tokyo (JP)

( * ) Notice: Subject to any disclaimer, the term of this patent is extended or adjusted under 35 U.S.C. 154(b) by 15 days.

(21) Appl. No.: 16/611,930

(22) PCT Filed: Apr. 4, 2018

(86) PCT No.: PCT/JP2018/014463
§ 371 (c)(1),
(2) Date: Nov. 8, 2019

(87) PCT Pub. No.: WO2018/211847
PCT Pub. Date: Nov. 22, 2018

(65) Prior Publication Data
US 2021/0145743 A1 May 20, 2021

(30) Foreign Application Priority Data
May 18, 2017 (JP) .............................. JP2017-099052

(51) Int. Cl.
*A61K 9/127* (2006.01)
*A61K 8/14* (2006.01)
(Continued)

(52) U.S. Cl.
CPC ............ *A61K 9/127* (2013.01); *A23D 7/0053* (2013.01); *A23D 7/011* (2013.01); *A61K 8/14* (2013.01);
(Continued)

(58) Field of Classification Search
CPC ........ A61K 9/127; A61K 8/14; A61K 31/341; A61K 31/405; A61K 31/436;
(Continued)

(56) References Cited

U.S. PATENT DOCUMENTS 6,605,298 B1 * 8/2003 Leigh .................. A61K 9/0014
264/4.1
2006/0233846 A1 10/2006 Leigh et al.

FOREIGN PATENT DOCUMENTS

JP S55-118419 A 9/1980
JP H10-500675 A 1/1998
(Continued)

OTHER PUBLICATIONS

International Search Report issued in corresponding International Patent Application No. PCT/JP2018/014463 dated Jul. 3, 2018.
(Continued)

*Primary Examiner* — Jianfeng Song
(74) *Attorney, Agent, or Firm* — Morgan, Lewis & Bockius LLP (57) ABSTRACT

The present invention relates to a self-emulsifiable composition including a monoacyl phospholipid, a diacyl phospholipid, oils and fats, and a polyhydric alcohol, in which the content ratio between the monoacyl phospholipid and the diacyl phospholipid is in the range of monoacyl phospholipid:diacyl phospholipid=1:9 to 9:1 as a mass ratio.

9 Claims, 1 Drawing Sheet

(51) Int. Cl.
| | |
|---|---|
| A61K 47/24 | (2006.01) |
| A61K 47/10 | (2017.01) |
| A61K 47/44 | (2017.01) |
| A61K 31/436 | (2006.01) |
| A61K 31/341 | (2006.01) |
| A61K 31/4422 | (2006.01) |
| A61K 31/405 | (2006.01) |
| A61K 38/13 | (2006.01) |
| A61Q 19/00 | (2006.01) |
| A23D 7/005 | (2006.01) |
| A23D 7/01 | (2006.01) |

(52) U.S. Cl.
CPC .......... *A61K 31/341* (2013.01); *A61K 31/405* (2013.01); *A61K 31/436* (2013.01); *A61K 31/4422* (2013.01); *A61K 38/13* (2013.01); *A61K 47/10* (2013.01); *A61K 47/24* (2013.01); *A61K 47/44* (2013.01); *A61Q 19/00* (2013.01); *A61K 2800/10* (2013.01); *A61K 2800/21* (2013.01)

(58) Field of Classification Search
CPC .. A61K 31/4422; A23D 7/0053; A23D 7/011; A61Q 19/00
See application file for complete search history.

(56) References Cited

FOREIGN PATENT DOCUMENTS

| | | | |
|---|---|---|---|
| JP | 2001-300284 A | 10/2001 | |
| JP | 2008-127327 A | 6/2008 | |
| JP | 2010-533714 A | 10/2010 | |
| JP | 2011-120604 A | 6/2011 | |
| JP | 2013-536805 A | 9/2013 | |
| WO | 95/31969 A1 | 11/1995 | |
| WO | 99/44642 A1 | 9/1999 | |
| WO | 00/61113 A1 | 10/2000 | |
| WO | WO-0061113 A1 * | 10/2000 | .......... A61K 9/1075 |
| WO | 02/078650 A1 | 10/2002 | |
| WO | 2009/011861 A1 | 1/2009 | |
| WO | 2012/028101 A1 | 3/2012 | |

OTHER PUBLICATIONS

International Preliminary Report on Patentability and Written Opinion issued in corresponding International Patent Application No. PCT/JP2018/014463 dated Nov. 28, 2019.

Suzuki et al., "Basics on Emulsion Technologies were Reviewed from the Following Viewpoints," Journal of Society of Cosmetic Chemists of Japan, 44:103-117 (2010) (see English abstract).

Extended European Search Report issued in counterpart European Patent Application No. 18801505.1 dated Jan. 21, 2021.

* cited by examiner

SELF-EMULSIFIABLE COMPOSITION, PRODUCTION METHOD THEREFOR, NANOEMULSION, AND PRODUCTION METHOD THEREFOR

TECHNICAL FIELD

The present invention relates to a self-emulsifiable composition, a method for producing the self-emulsifiable composition, a nanoemulsion, and a method for producing the nanoemulsion.

BACKGROUND ART

Regarding a method for solubilizing a sparingly soluble substance, methods of forming a fine emulsion are known. As the methods of fainting a fine emulsion, a method of performing a high-pressure emulsification treatment, a method of using a synthetic surfactant (polyoxyethylene sorbitan oleate (Tween 80) or the like) (for example, Patent Literature 1), and a method of using a phospholipid (for example, Patent Literatures 2 and 3) are conventionally known.

CITATION LIST

Patent Literature

Patent Literature 1: Japanese Unexamined Patent Publication No. 2011-120604
Patent Literature 2: Japanese Unexamined Patent Publication No. H10-500675
Patent Literature 3: Japanese Unexamined Patent Publication No. 2013-536805

SUMMARY OF INVENTION

Problems to be Solved by the Invention

The method based on a high-pressure emulsification treatment has a problem that it is difficult to obtain an emulsion having a nano (nm)-scale average particle size, deterioration of the mixing raw materials proceeds during the treatment, and the industrial production requires high cost in terms of time and price.

In the method of using a synthetic surfactant, a self-emulsifiable composition that can produce an emulsion having a nanoscale average particle size by adding water, can be obtained. On the other hand, since synthetic surfactants have insufficient biocompatibility, there is a possibility that the synthetic surfactants may cause serious side effects after administration, or the like. Thus, the method is not suitable for use applications that are accompanied by administration into a human body.

In the method of using a phospholipid, a self-emulsifiable composition can be obtained; however, in order to completely dissolve the phospholipid, it is essential to use an organic solvent such as a lower alcohol. Since this organic solvent is harmful to the human body, there is a possibility that the organic solvent may cause side effects after administration, or the like. Thus, the method is not suitable for use applications that are accompanied by administration into a human body.

Thus, it is an object of the present invention to provide a self-emulsifiable composition formed only from raw materials that are highly safe to the human body, the self-emulsifiable composition being capable of producing a nanoemulsion having a sparingly soluble substance solubilized therein by a simple operation, and a method for producing the self-emulsifiable composition. It is another object of the present invention to provide a method for producing a nanoemulsion using a self-emulsifiable composition, and a nanoemulsion obtainable by the production method.

Means for Solving the Problems

The inventor of the present invention found that when a phospholipid (diacyl phospholipid) is used in combination with a lysophospholipid (monoacyl phospholipid), solubility of the phospholipid is increased, and a self-emulsifiable composition is obtained even without using an organic solvent such as a lower alcohol, and that this composition can produce a nanoemulsion with a simple and easy operation such as addition of an aqueous solution. The present invention is based on these novel findings.

That is, the present invention relates to, for example, the following respective inventions.

(1) A self-emulsifiable composition including a monoacyl phospholipid, a diacyl phospholipid, oils and fats, and a polyhydric alcohol, in which the content ratio between the monoacyl phospholipid and the diacyl phospholipid is in the range of monoacyl phospholipid:diacyl phospholipid=1:9 to 9:1 as a mass ratio.

(2) The self-emulsifiable composition as described in (1), in which when the total content of the monoacyl phospholipid and the diacyl phospholipid is designated as x % by mass, the content of the oils and fats is designated as y % by mass, and the content of the polyhydric alcohol is designated as z % by mass, with respect to 100% by mass of the total content of the monoacyl phospholipid, the diacyl phospholipid, the oils and fats, and the polyhydric alcohol, x, y, and z are within a region surrounded by a triangle having the following points A, B, and C in a triangular diagram (x, y, z) as apexes:
A: (x, y, z)=(0.1, 0.1, 99.8)
B: (x, y, z)=(65.0, 0.1, 34.9)
C: (x, y, z)=(45.0, 40.0, 15.0).

(3) The self-emulsifiable composition as described in (1) or (2), further containing a sparingly soluble substance.

(4) The self-emulsifiable composition as described in any one of (1) to (3), in which the average particle size obtainable when the self-emulsifiable composition is mixed with a 10-fold volume of water is 250 nm or less.

(5) The self-emulsifiable composition as described in any one of (1) to (4), in which the content of ethanol is 15% by mass or less.

(6) The self-emulsifiable composition as described in any one of (1) to (5), in which the total content of the monoacyl phospholipid and the diacyl phospholipid is from 0.1% by mass to 70% by mass.

(7) The self-emulsifiable composition as described in any one of (1) to (6), in which the content of a synthetic surfactant is 10% by mass or less.

(8) The self-emulsifiable composition as described in any one of (1) to (7), in which the oils and fats include medium-chain fatty acids.

(9) The self-emulsifiable composition as described in any one of (1) to (8), in which the content of the oils and fats satisfies the requirement of being from 0.1% by mass to 35% by mass based on the total amount of the composition, or being from 0.1 part by mass to 70 parts by mass with respect to 100 parts by mass of the total content of the monoacyl phospholipid and the diacyl phospholipid.

(10) The self-emulsifiable composition as described in any one of (1) to (9), in which the content of the polyhydric alcohol is from 20% by mass to 99% by mass based on the total amount of the composition.

(11) A method for producing a self-emulsifiable composition, the method including: a step of dissolving raw materials including a monoacyl phospholipid, a diacyl phospholipid, oils and fats, and a polyhydric alcohol in a volatile organic solvent; and a step of removing the organic solvent after the dissolution, in which the content ratio between the monoacyl phospholipid and the diacyl phospholipid is in the range of monoacyl phospholipid:diacyl phospholipid=1:9 to 9:1 as a mass ratio.

(12) A method for producing a self-emulsifiable composition, the method including a step of mixing raw materials including a monoacyl phospholipid, a diacyl phospholipid, oils and fats, and a polyhydric alcohol, and heating and stirring the mixture, in which the content ratio between the monoacyl phospholipid and the diacyl phospholipid is in the range of monoacyl phospholipid:diacyl phospholipid=1:9 to 9:1 as a mass ratio.

(13) A method for producing a nanoemulsion, the method including a step of mixing the self-emulsifiable composition as described in any one of (1) to (10) with an aqueous solution.

(14) A nanoemulsion having a sparingly soluble substance solubilized therein, the nanoemulsion including a sparingly soluble substance, a monoacyl phospholipid, a diacyl phospholipid, oils and fats, and a polyhydric alcohol, in which the content ratio between the monoacyl phospholipid and the diacyl phospholipid is in the range of monoacyl phospholipid:diacyl phospholipid=1:9 to 9:1 as a mass ratio, and the average particle size is 250 nm or less.

(15) The nanoemulsion as described in (14), which is a pharmaceutical product.

(16) The nanoemulsion as described in (14), which is a cosmetic product.

(17) The nanoemulsion as described in (14), which is a food product.

Effects of the Invention

According to the present invention, there are provided a self-emulsifiable composition formed only from raw materials that are highly safe to the human body, the self-emulsifiable composition being capable of producing a nanoemulsion having a sparingly soluble substance solubilized therein by a simple operation, and a method for producing the self-emulsifiable composition.

According to the present invention, there are also provided a method for producing a nanoemulsion using the self-emulsifiable composition, and a nanoemulsion obtainable by the production method.

EMBODIMENTS FOR CARRYING OUT THE INVENTION

Hereinafter, embodiments for carrying out the present invention will be described in detail. However, the present invention is not intended to be limited to the following embodiments.

<Features of Present Invention>
(Self-Emulsifiable Composition)

The present invention has a feature of providing a self-emulsifiable composition including a monoacyl phospholipid, a diacyl phospholipid, oils and fats, and a polyhydric alcohol, in which the content ratio between the monoacyl phospholipid and the diacyl phospholipid is in the range of monoacyl phospholipid:diacyl phospholipid=1:9 to 9:1 as a mass ratio.

(Method for Producing Self-Emulsifiable Composition)

The present invention also has a feature of providing a method for producing a self-emulsifiable composition, the method including a step of dissolving raw materials including a monoacyl phospholipid, a diacyl phospholipid, oils and fats, and a polyhydric alcohol in a volatile organic solvent, and a step of removing the organic solvent after dissolution, in which the content ratio between the monoacyl phospholipid and the diacyl phospholipid is in the range of monoacyl phospholipid:diacyl phospholipid=1:9 to 9:1 as a mass ratio, and a method for producing a self-emulsifiable composition, the method including a step of mixing raw materials including a monoacyl phospholipid, a diacyl phospholipid, oils and fats, and a polyhydric alcohol, and heating and stirring the mixture, in which the content ratio between the monoacyl phospholipid and the diacyl phospholipid is in the range of monoacyl phospholipid:diacyl phospholipid=1:9 to 9:1 as a mass ratio.

(Nanoemulsion)

The present invention further has a feature of providing a nanoemulsion having a sparingly soluble substance solubilized therein, the nanoemulsion including a sparingly soluble substance, a monoacyl phospholipid, a diacyl phospholipid, oils and fats, and a polyhydric alcohol, in which the content ratio between the monoacyl phospholipid and the diacyl phospholipid is in the range of monoacyl phospholipid:diacyl phospholipid=1:9 to 9:1 as a mass ratio, and the average particle size is 250 nm or less.

(Method for producing nanoemulsion) The present invention further has a feature of providing a method for producing a nanoemulsion, the method including a step of mixing the self-emulsifiable composition according to the present invention with an aqueous solution.

<Nanoemulsion>

According to the present specification, the term "nanoemulsion" means a composition in the form of an emulsion having an average particle size of more than 0 nm and less than or equal to 1,000 nm.

<Average Particle Size>

According to the present specification, the term "average particle size" means the volume-based average particle size measured by a dynamic light scattering method. The average particle size can be measured using a measuring apparatus that utilized a dynamic light scattering method (for example, a particle size distribution analyzer (for example, Coulter N4 Plus submicron particle size distribution analyzer, manufactured by Beckman Coulter, Inc.)).

<Monoacyl Phospholipid>

According to the present specification, the "monoacyl phospholipid" means a lysophospholipid, which is a phospholipid having one fatty acid come off. The monoacyl phospholipid includes a lysosphingophospholipid, which is obtained as the fatty acid that is amide-bonded to an amino group of the sphingosine skeleton has come off from a sphingophospholipid, and a monoacylglycerophospholipid, which is obtained as any one of the fatty acids that are ester-bonded to a hydroxyl group at the 1-position or the 2-position of the glycerol skeleton has come off from a glycerophospholipid.

Examples of the monoacyl phospholipid include lysophosphatidic acid, lysophosphatidylcholine, lysophosphatidylethanolamine, lysophosphatidylinositol, lysophosphatidylserine, lysophosphatidylglycerol, and lysosphingomyelin. The monoacyl phospholipid is preferably lysophosphatidylcholine, from the viewpoint of further increasing the solubility of the diacyl phospholipid. The monoacyl phospholipids may be used singly or in combination of two or more kinds thereof. The monoacyl phospholipid may be incorporated in the form of a composition including a monoacyl phospholipid as a main component.

Monoacyl phospholipids can be obtained according to conventional methods. Specifically, monoacyl phospholipids can be obtained by, for example, treating phospholipids extracted from animal and plant raw materials such as egg yolk, soybean, or rapeseed, with enzymes such as a phospholipase and a ceramide deacylase; or by treating animal and plant raw materials directly with enzymes such as a phospholipase and a ceramide deacylase, and then extracting the monoacyl phospholipids with a solvent such as ethanol. The monoacyl phospholipids may be products that have been subjected to a hydrogenation treatment as necessary.

Regarding the monoacyl phospholipid, it is preferable to use an egg yolk-derived lysophospholipid from the viewpoint of further increasing the solubility of the diacyl phospholipid. Egg yolk-derived lysophospholipids have a larger content of lysophosphatidylcholine and lower contents of lysophosphatidylethanolamine and lysophosphatidylinositol.

<Diacyl Phospholipid>

A diacyl phospholipid includes a sphingophospholipid and a diacylglycerophospholipid. Examples of the diacyl phospholipid include phosphatidic acid, phosphatidylcholine, phosphatidylethanolamine, phosphatidylinositol, phosphatidylserine, phosphatidylglycerol, and sphingomyelin. The diacyl phospholipids may be used singly or in combination of two or more kinds thereof. The diacyl phospholipid may be incorporated in the form of a composition including a diacyl phospholipid as a main component.

Diacyl phospholipids can be obtained according to conventional methods. Specifically, the diacyl phospholipids can be obtained by, for example, extracting the diacyl phospholipids from animal and plant raw materials such as egg yolk, soybean, or rapeseed. The diacyl phospholipids may be products that have been subjected to a hydrogenation treatment as necessary.

Regarding the diacyl phospholipid, for example, phospholipids derived from animal and plant raw materials such as egg yolk, soybean, or rapeseed can be used without any particular limitations.

<Content Ratio of Monoacyl Phospholipid and Diacyl Phospholipid>

The self-emulsifiable composition related to the present embodiment can dissolve a diacyl phospholipid by using a monoacyl phospholipid together with a diacyl phospholipid, even without using an organic solvent such as a lower alcohol. The content ratio between the monoacyl phospholipid and the diacyl phospholipid in the self-emulsifiable composition according to the present embodiment may be in the range of monoacyl phospholipid:diacyl phospholipid=1:9 to 9:1 as a mass ratio. From the viewpoint of providing the above-described effects more noticeably, the content ratio is preferably in the range of monoacyl phospholipid:diacyl phospholipid=1:3 to 3:1 as a mass ratio.

<Content of Monoacyl Phospholipid and Diacyl Phospholipid>

The total content of the monoacyl phospholipid and the diacyl phospholipid in the self-emulsifiable composition according to the present embodiment is not particularly limited; however, for example, the total content may be from 0.1% by mass to 70% by mass based on the total amount of the composition. When the total content of the monoacyl phospholipid and the diacyl phospholipid is in this range, a self-emulsifiable composition that can produce a nanoemulsion by a simple operation such as addition of an aqueous solution can be suitably obtained. From a similar viewpoint, the total content of the monoacyl phospholipid and the diacyl phospholipid may be from 0.1% by mass to 65% by mass, may be from 5% by mass to 55% by mass, or may be from 10% by mass to 45% by mass, based on the total amount of the composition.

<Oils and Fats>

The oils and fats that are used for the self-emulsifiable composition according to the present embodiment are not particularly limited. Examples of the oils and fats include plant oils such as soybean oil, sesame oil, rapeseed oil, safflower oil, olive oil, castor oil, corn oil, cotton seed oil, rice oil, sunflower oil, grape seed oil, and wheat germ oil; and medium-chain fatty acid triglycerides (MCT). Among these, from the viewpoint that it is easy to maintain a state of being self-emulsifiable, the oils and fats are preferably medium-chain fatty acid triglycerides (MCT).

<Content of Oils and Fats>

The content of the oils and fats in the self-emulsifiable composition according to the present embodiment is not particularly limited; however, for example, the content may be from 0.1% by mass to 35% by mass based on the total amount of the composition. Usually, when the content of the oils and fats is not 10% by mass or less, a transparent composition cannot be obtained; however, the self-emulsifiable composition according to the present invention can be made into a transparent composition even when the content of the oils and fats is within the above-described range. Furthermore, when the content of the oils and fats is within this range, a self-emulsifiable composition that can produce a nanoemulsion by a simple operation such as addition of an aqueous solution can be suitably obtained. From a similar viewpoint, the content of the oils and fats may be from 0.1% by mass to 30% by mass, may be from 0.1% by mass to 25% by mass, or may be from 0.1% by mass to 15% by mass, based on the total amount of the composition.

From a different viewpoint, the content of the oils and fats in the self-emulsifiable composition according to the present embodiment may be, for example, from 0.1 part by mass to 70 parts by mass with respect to 100 parts by mass of the total content of the monoacyl phospholipid and the diacyl phospholipid. Thereby, an effect that a fine emulsion is formed is provided more noticeably. From a similar viewpoint, the content of the oils and fats may be from 1 part by mass to 70 parts by mass, may be from 5 parts by mass to 65 parts by mass, may be from 10 parts by mass to 60 parts by mass, or may be from 20 parts by mass to 55 parts by mass, with respect to 100 parts by mass of the total content of the monoacyl phospholipid and the diacyl phospholipid.

<Polyhydric Alcohol>

A polyhydric alcohol is an alcohol having two or more hydroxyl groups in the molecule. The polyhydric alcohol used for the self-emulsifiable composition according to the present embodiment is not particularly limited; however, examples include 1,3-butanediol, 1,3-propanediol, 3-methyl-1,3-butanediol, propylene glycol, dipropylene glycol, polypropylene glycol, butylene glycol, 1,2-pentanediol, ethylene glycol, diethylene glycol, triethylene glycol, polyethylene glycol, polyoxyethylene glycol, glycerin, polyglycerin (for example, diglycerin and tetraglycerin), xylytol, maltitol, pentaerythritol, sorbitol, and trehalose. Among these, from the viewpoint of safety to the human body, glycerin, propylene glycol, and butylene glycol are preferred.

<Content of Polyhydric Alcohol>

The content of the polyhydric alcohol in the self-emulsifiable composition according to the present embodiment is not particularly limited; however, for example, the content may be from 20% by mass to 99% by mass based on the total amount of the composition. When the content of the polyhydric alcohol is within this range, a self-emulsifiable composition that can produce a nanoemulsion by a simple operation such as addition of an aqueous solution can be suitably obtained. From a similar viewpoint, the content of the polyhydric alcohol may be from 30% by mass to 95% by mass, or may be from 40% by mass to 90% by mass, based on the total amount of the composition.

<Contents of Phospholipids, Oils and Fats, and Polyhydric Alcohol>

(Relative Contents of Phospholipids, Oils and Fats, and Polyhydric Alcohol)

Figure 1:
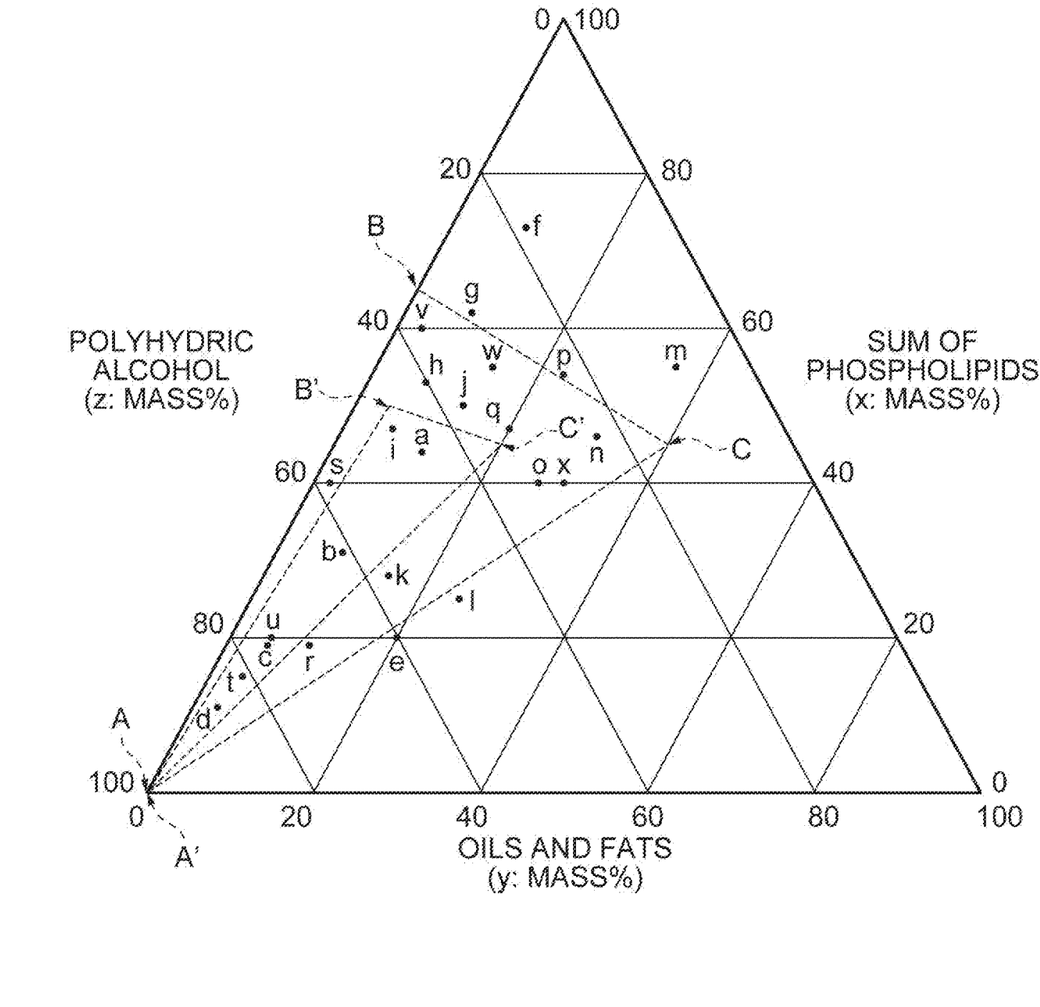
FIG. 1 is a triangular diagram showing the composition of a self-emulsifiable composition prepared in Test Example 3.

The self-emulsifiable composition according to the present embodiment is preferably such that when the total content of the monoacyl phospholipid and the diacyl phospholipid is designated as x % by mass, the content of the oils and fats is designated as y % by mass, and the content of the polyhydric alcohol is designated as z % by mass, with respect to 100% by mass of the total content of the monoacyl phospholipid, diacyl phospholipid, oils and fats, and polyhydric alcohol, x, y, and z are within a region surrounded by a triangle having point A (x, y, z)=(0.1, 0.1, 99.8), point B (x, y, z)=(65.0, 0.1, 34.9), and point C (x, y, z)=(45.0, 40.0, 15.0) in a triangular diagram (x, y, z) as apexes (see FIG. 1). When the contents of the phospholipids (monoacyl phospholipid and diacyl phospholipid), the oils and fats, and the polyhydric alcohol are within this range, for example, a nanoemulsion having an average particle size of 250 nm or less can be produced by adding a 10-fold volume of water. The nanoemulsion having an average particle size of 250 nm or less is suitably used as, for example, a pharmaceutical product such as an injectable preparation.

FIG. 1 is a triangular diagram showing the composition of a self-emulsifiable composition prepared in Test Example 3 that will be described below. Regarding the triangular diagram shown in FIG. 1, the respective sides correspond to the total content (x % by mass) of the monoacyl phospholipid and the diacyl phospholipid, the content of the oils and fats (y % by mass), and the content of the polyhydric alcohol (z % by mass), with respect to 100% by mass of the total content of the monoacyl phospholipid, diacyl phospholipid, oils and fats, and polyhydric alcohol. In FIG. 1, the points represented by A, B, and C correspond to point A (x, y, z)=(0.1, 0.1, 99.8), point B (x, y, z)=(65.0, 0.1, 34.9), and point C (x, y, z)=(45.0, 40.0, 15.0), and a region surrounded by a triangle having A, B, and C as apexes (including the boundary lines) represents the above-mentioned range.

The self-emulsifiable composition according to the present embodiment is more preferably such that x, y, and z are within a region surrounded by a triangle having point A' (x, y, z)=(0.1, 0.1, 99.8), point B' (x, y, z)=(50.0, 4.1, 45.9), and point C' (x, y, z)=(45.0, 20.0, 35.0) in a triangular diagram (x, y, z) as apexes (see FIG. 1). When the contents of the phospholipids (monoacyl phospholipid and diacyl phospholipid), oils and fats, and polyhydric alcohol are within this range, for example, a nanoemulsion having an average particle size of 100 nm or less can be easily produced by addition of a 10-fold volume of water.

(Contents of Phospholipids, Oils and Fats, and Polyhydric Alcohol)

The total content of the monoacyl phospholipid, diacyl phospholipid, oils and fats, and polyhydric alcohol in the self-emulsifiable composition according to the present embodiment is not particularly limited; however, for example, the total content is usually from 1% by mass to 100% by mass based on the total amount of the composition. When the total content of the monoacyl phospholipid, diacyl phospholipid, oils and fats, and polyhydric alcohol is in this range, a self-emulsifiable composition that can produce a nanoemulsion by a simple operation such as addition of an aqueous solution can be suitably obtained. From a similar viewpoint, the total content of the monoacyl phospholipid, diacyl phospholipid, oils and fats, and polyhydric alcohol may be from 10% by mass to 100% by mass based on the total amount of the composition.

<Ethanol Content>

The self-emulsifiable composition according to the present embodiment can dissolve a diacyl phospholipid by using a monoacyl phospholipid together with a diacyl phospholipid in combination, even without using an organic solvent such as ethanol. Therefore, the content of ethanol in the self-emulsifiable composition according to the present embodiment may be 15% by mass or less, preferably 10% by mass or less, more preferably 5% by mass or less, and even more preferably 0.2% by mass or less, based on the total amount of the composition.

<Content of Synthetic Surfactant>

The self-emulsifiable composition according to the present embodiment can produce a nanoemulsion without using a synthetic surfactant. Therefore, the content of a synthetic surfactant in the self-emulsifiable composition according to the present embodiment may be 10% by mass or less, preferably 5% by mass or less, and more preferably 1% by mass or less, based on the total amount of the composition. Examples of the synthetic surfactant include polyoxyethylene hardened castor oil (for example, manufactured by Nikko Chemicals Co., Ltd., NIKKOL HCO-60), and polysorbate (for example, manufactured by NOF CORPORATION, POLYSORBATE 80HX2).

<Water Content>

The content of water included in the self-emulsifiable composition according to the present embodiment is not particularly limited; however, the content may be less than 50% by mass based on the total amount of the composition. From the viewpoint that a state of being self-emulsifiable can be easily maintained, the content of water is preferably less than 20% by mass, more preferably less than 10% by mass, and even more preferably less than 5% by mass. When the content of water is less than 5% by mass, a substantially non-water-based composition is obtained, and this can be suitably used as a pharmaceutical product.

<Sparingly Soluble Substance>

Since the self-emulsifiable composition according to the present embodiment can be produced into a solubilized preparation by incorporating various sparingly soluble substances, the self-emulsifiable composition may further contain a sparingly soluble substance. The term sparingly soluble substance means a substance having low solubility in water, and specifically, the term means a substance whose solubility according to the Japanese Pharmacopoeia, the 16$^{th}$ Edition, is "slightly hard to dissolve" (the amount of a solvent required to dissolve 1 g or 1 mL of a solute is more than or equal to 30 mL and less than 100 mL), "hard to dissolve" (the amount of the same solvent is more than or equal to 100 mL and less than 1,000 mL), "very hard to dissolve" (the amount of the same solvent is more than or equal to 1,000 mL and less than 10,000 mL), or "almost does not dissolve" (the amount of the same solvent is 10,000 mL or more).

Examples of the sparingly soluble substance include docetaxel, paclitaxel, capecitabine, oxaliplatin, geftinat, doxorubicin, irinotecan, gemcitabine, pemetrexed, temozolomide, imatinib, vinorelbine, letrozole, teniposide, etoposide, podophyllotoxin, camptothecin, 10-hydroxycamptothecin, 9-hydroxycamptothecin, 7-ethyl-10-hydroxycamptothecin, topotecan, irinotecan, vinblastine, vincristine, vindesine, vinflunine, vinpocetine, norcantharidin, silybin, propofol, florfenicol, mitiglinide, artemisinin, dihydroartemisinin, sirolimus, ibuprofen, nitrendipine, nicardipine, nimodipine, gliclazide, propulsid, felodipine, glibenclamide, acyclovir, oleanolic acid, breviscapine, ferulic acid, paracetamol, palmitoylrhizoxin, penclomedine, tamoxifen, navelbine, valproic acid, tacrolimus, cyclosporine A, amphotericin B, ketoconazole, domperidone, sulpiride, fenofibrate, bezafibrate, azithromycin, itraconazole, miconazole, brimonidine, latanoprost, silybin, erythromycin, roxithromycin, rifaximin, cisapride, cyclosporine, diclofenac acid, felodipine, ibuprofen, indomethacin, acemetacin, nicardipine, nifedipine, terfenadine, theophylline, ketoprofen, furosemide, spironolactone, dipyridamole, piroxicam, mefenamic acid, trichlorothiazide, pindolol, oil-soluble vitamins (for example, vitamin A and vitamin E), carotenoids (for example, lycopene, chlorophyll, lutein, zeaxanthin, astaxanthin, and fucoxanthin), polyphenols (for example, flavonols, flavanones, flavones, isoflavones, phenol carboxylic acids, anthocyanidins, hydroxycinnamic acid derivatives, ellagic acid, and the like), and co-enzyme Q10. The sparingly soluble substances may be used singly, or two or more kinds thereof may be used in combination.

<Self-Emulsifiable Composition>

The self-emulsifiable composition according to the present invention is in a state called O/D phase (the oil phase and the aqueous phase are both continuous phases, and the composition is also referred to as bi-continuous nanoemulsion), or in a state equivalent thereto, and the external appearance is transparent. When water is added to this composition, phase transition occurs, and an O/W type nanoemulsion is produced.

<Average Particle Size Obtainable when Mixed with 10-Fold Volume of Water>

The self-emulsifiable composition according to the present invention is such that when the composition is mixed with a 10-fold volume of water, the average particle size becomes greater than 0 nm and less than or equal to 1,000 nm. Regarding a self-emulsifiable composition according to an embodiment, the average particle size obtainable when the composition is mixed with a 10-fold volume of water is preferably 250 nm or less, more preferably 100 nm or less, and even more preferably 30 nm or less. When the average particle size is in the range of 250 nm or less, for example, the self-emulsifiable composition can be suitably used as a pharmaceutical product such as an injectable preparation. This average particle size can be controlled by adjusting the relative contents and the like of the phospholipids, the oils and fats, and the polyhydric alcohol, as described above.

<Method for Producing Self-Emulsifiable Composition>

The production method according to the present embodiment includes a step of dissolving raw materials including a monoacyl phospholipid, a diacyl phospholipid, oils and fats, and a polyhydric alcohol in a volatile organic solvent (hereinafter, also referred to as "dissolving step") and a step of removing the organic solvent after the dissolution (hereinafter, also referred to as "removal step").

The production method according to another embodiment includes a step of mixing raw materials including a monoacyl phospholipid, a diacyl phospholipid, oils and fats, and a polyhydric alcohol, and heating and stirring the mixture (hereinafter, also referred to as "heating and stirring step").

(Raw Materials)

The raw materials used in the dissolving step include at least a monoacyl phospholipid, a diacyl phospholipid, oils and fats, and a polyhydric alcohol. The raw materials may further include water, a sparingly soluble substance, and the like. The respective contents and the like of the monoacyl phospholipid, diacyl phospholipid, oils and fats, and polyhydric alcohol among the raw materials are similar to the respective contents and the like in the self-emulsifiable composition according to the present embodiment described above.

(Volatile Organic Solvent)

The volatile organic solvent used in the dissolving step is not particularly limited as long as it is an organic solvent that is capable of dissolving the raw materials and can be removed in the removal step. Examples of the volatile organic solvent include methanol, ethanol, isopropanol, normal hexane, diethyl ether, tetrahydrofuran, and chloroform.

(Dissolving Step)

The dissolving step can be carried out, for example, at a temperature of from 25° C. to 70° C., and preferably from 30° C. to 60° C., for a period of from 1 minute to 30 minutes, and preferably from 3 minutes to 10 minutes. The dissolving step may be carried out while the raw materials and the volatile organic solvent are stirred.

(Removal Step)

The removal step can be carried out by any arbitrary method as long as a method capable of removing the volatile organic solvent is used. Specifically, for example, the removal step can be carried out by a method of distilling off the volatile organic solvent under reduced pressure using a rotary evaporator or the like, or a method of evaporating the volatile organic solvent by heating. When the removal step is implemented, a self-emulsifiable composition that is in a state called O/D phase, or a state equivalent thereto, is obtained.

(Heating and Stirring Step)

The heating and stirring step can be carried out, for example, at a temperature of from 25° C. to 90° C., and preferably from 50° C. to 80° C., for a period of from 1 minute to 60 minutes, and preferably from 5 minutes to 30 minutes. When the heating and stirring step is implemented, a self-emulsifiable composition that is in a state called O/D phase, or a state equivalent thereto, is obtained.

(Production of Self-Emulsifiable Composition Containing Sparingly Soluble Substance)

In a case in which a self-emulsifiable composition containing a sparingly soluble substance is produced, for example, the sparingly soluble substance may be incorporated into the raw materials, or the above-described dissolving step and removal step may be carried out by using a mixture obtained by adding a self-emulsifiable composition that has been subjected to the removal step or the heating and stirring step to the sparingly soluble substance, as a raw material.

<Method for Producing Nanoemulsion>

The method for producing a nanoemulsion according to the present embodiment includes a step of mixing the self-emulsifiable composition according to the present invention with an aqueous solution (hereinafter, also referred to as "mixing step"). The self-emulsifiable composition may contain a sparingly soluble substance.

(Type of Aqueous Solution)

The type of the aqueous solution that is added in the mixing step can be selected as appropriate according to the use application or the like of the nanoemulsion to be produced, and specific examples include water, physiological saline, a buffer solution (for example, PBS), a glucose solution, and a Ringer's solution.

(Amount of Addition of Aqueous Solution)

The amount of the aqueous solution to be added in the mixing step is not particularly limited and can be selected as appropriate according to the use application or the like of the nanoemulsion to be produced. Specifically, for example, the amount of the aqueous solution may be one time in volume, three times in volume, five times in volume, or ten times in volume, with respect to the volume of the self-emulsifiable composition.

(Mixing Step)

The mixing step can be carried out by, for example, by adding an aqueous solution to the self-emulsifiable composition according to the present invention. In the mixing step, stirring may be performed after the aqueous solution is added.

<Nanoemulsion>

The nanoemulsion according to the present embodiment includes a sparingly soluble substance, a monoacyl phospholipid, a diacyl phospholipid, oils and fats, and a polyhydric alcohol, and the content ratio between the monoacyl phospholipid and the diacyl phospholipid is in the range of monoacyl phospholipid:diacyl phospholipid=1:9 to 9:1 as a mass ratio, while the average particle size is 250 nm or less. The respective contents and the like of the sparingly soluble substance, monoacyl phospholipid, diacyl phospholipid, oils and fats, and polyhydric alcohol are similar to the respective contents and the like in the self-emulsifiable composition according to the present embodiment described above.

<Average Particle Size of Nanoemulsion>

The average particle size of the nanoemulsion according to the present embodiment may be 250 nm or less, more preferably 200 nm or less, even more preferably 150 nm or less, still more preferably 100 nm or less, and particularly preferably 30 nm or less. When the average particle size of the nanoemulsion is within this range, the nanoemulsion can be suitably used as, for example, a pharmaceutical product such as an injectable preparation.

<Use Applications of Nanoemulsion>

Since the nanoemulsion according to the present embodiment has a sparingly soluble substance solubilized therein, the nanoemulsion can be used for a variety of use applications. Specifically, for example, the nanoemulsion can be used as a food product such as a supplement, a pharmaceutical product (for example, an oral preparation or an injectable preparation), or a cosmetic product such as a cleansing oil. The nanoemulsion according to the present embodiment may be supplied as an emulsion that has been produced in advance, or may be supplied as a self-emulsifiable composition according to the present invention and then prepared at the time of use.

EXAMPLES

Hereinafter, the present invention will be described more specifically based on Examples and the like. However, the present invention is not intended to be limited to the following Examples.

Test Example 1: Preparation and Evaluation of Self-Emulsifiable Composition (1)

An egg yolk-derived monoacyl phospholipid (egg yolk lysolecithin LPC-1, manufactured by Kewpie Corporation), an egg yolk-derived diacyl phospholipid (egg yolk lecithin PL-100M, manufactured by Kewpie Corporation), concentrated glycerin (concentrated glycerin of Japanese Pharmacopoeia, manufactured by Sakamoto Yakuhin Kogyo Co., Ltd.), and medium-chain fatty acids (COCONARD RK, manufactured by Kao Corporation) were blended according to the compositions indicated in Table 1, and thus self-emulsifiable compositions No. 1 to No. 15 were prepared.

Specifically, medium-chain fatty acids, an egg yolk-derived diacyl phospholipid, an egg yolk-derived monoacyl phospholipid, and concentrated glycerin were added to a 200-mL pear-shaped flask, and then 20 mL of ethanol was further added thereto. This was warmed for 5 minutes in a warm bath at 60° C. and dissolved. Next, ethanol was distilled off using a rotary evaporator, and thus a self-emulsifiable composition was obtained.

The ethanol content in the self-emulsifiable composition thus obtained was measured by loss on drying.

To 0.5 mL of the self-emulsifiable composition thus obtained, a 10-fold volume of water, that is, 5 mL, was added, and thereby a nanoemulsion was produced. Measurement of the average particle size of the nanoemulsion was carried out using a measuring apparatus that utilized a dynamic light scattering method (Coulter N4 Plus submicron particle size distribution analyzer, manufactured by Beckman Coulter, Inc.), and the average particle size was determined as a volume-reduced value. The results are presented together in Table 1.

TABLE 1

| Blend | Monoacyl type:diacyl type = 3:1 | | | | | | Monoacyl type:diacyl type = 1:1 | | | | | Monoacyl type:diacyl type = 1:3 | | | |
| --- | --- | --- | --- | --- | --- | --- | --- | --- | --- | --- | --- | --- | --- | --- | --- |
| | No. 1 | No. 2 | No. 3 | No. 4 | No. 5 | No. 6 | No. 7 | No. 8 | No. 9 | No. 10 | No. 11 | No. 12 | No. 13 | No. 14 | No. 15 |
| Egg yolk-derived monoacyl phospholipid (g) | 1.5 | 1.5 | 2.25 | 2.25 | 3.0 | 1.0 | 1.0 | 1.0 | 1.0 | 1.0 | 1.5 | 0.5 | 0.5 | 0.5 | 0.5 |
| Egg yolk-derived diacyl phospholipid (g) | 0.5 | 0.5 | 0.75 | 0.75 | 1.0 | 1.0 | 1.0 | 1.0 | 1.0 | 1.0 | 1.5 | 1.5 | 1.5 | 1.5 | 1.5 |
| Polyhydric alcohol (concentrated glycerin) (g) | 2.0 | 4.0 | 4.0 | 5.0 | 3.0 | 2.0 | 4.0 | 6.0 | 8.0 | 16 | 5.0 | 2.0 | 4.0 | 8.0 | 16 |
| Oils and fats (medium-chain fatty acids) (g) | 0.5 | 0.5 | 2.0 | 2.0 | 2.0 | 0.5 | 0.5 | 2.0 | 0.5 | 0.5 | 2.0 | 0.5 | 0.5 | 0.5 | 0.5 |

TABLE 1-continued

| Blend | Monoacyl type:diacyl type = 3:1 | | | | | | Monoacyl type:diacyl type = 1:1 | | | | | Monoacyl type:diacyl type = 1:3 | | | |
| --- | --- | --- | --- | --- | --- | --- | --- | --- | --- | --- | --- | --- | --- | --- | --- |
| | No. 1 | No. 2 | No. 3 | No. 4 | No. 5 | No. 6 | No. 7 | No. 8 | No. 9 | No. 10 | No. 11 | No. 12 | No. 13 | No. 14 | No. 15 |
| Content of phospholipids (mass %) | 44 | 30 | 30 | 30 | 40 | 44 | 30 | 20 | 19 | 11 | 30.0 | 44 | 30 | 19 | 11 |
| Content of ethanol (mass %) | 0 | 0 | 0 | 0 | 0 | 0 | 0 | 0 | 0 | 0 | 0 | 0 | 0 | 0 | 0 |
| Average particle size of nanoemulsion after addition of water (nm) | 19 | 346 | 385 | 298 | 480 | 209 | 24 | 570 | 28 | ND*[1] | 389 | 192 | 211 | 163 | 161 |

*[1]ND: Below measurement limit.

When the egg yolk-derived monoacyl phospholipid was used in combination with the egg yolk-derived diacyl phospholipid, it was possible to dissolve the egg yolk-derived diacyl phospholipid, even without incorporating ethanol. Furthermore, all of the compositions thus obtained could produce nanoemulsions through a simple operation such as addition of water.

Test Example 2: Preparation and Evaluation of Self-Emulsifiable Composition Containing Sparingly Soluble Drug (1)

As sparingly soluble substances, nifedipine (solubility: "almost not soluble"), furosemide (solubility: "almost not soluble"), acemetacin (solubility: "almost not soluble"), and tacrolimus (solubility: "almost not soluble"), all of which are sparingly soluble drugs, were used. First, a self-emulsifiable composition was obtained according to the composition indicated in Table 2 by an operation similar to that of Test Example 1. Next, 5 g of the self-emulsifiable composition thus obtained was added to 50 mg of a sparingly soluble substance, and about 10 mL of ethanol was further added thereto. This was warmed for 5 minutes in a warm bath at 60° C., and thereby the sparingly soluble substance was dissolved. Next, ethanol was distilled off using a rotary evaporator, and thereby a self-emulsifiable composition containing the sparingly soluble substance was obtained.

TABLE 2

| Blend | |
| --- | --- |
| Egg yolk-derived monoacyl phospholipid (g) | 8.0 |
| Egg yolk-derived diacyl phospholipid (g) | 8.0 |
| Polyhydric alcohol (concentrated glycerin) (g) | 34.0 |
| Oils and fats (medium-chain fatty acids) (g) | 4.0 |
| Content of phospholipids (mass %) | 30 |
| Content of ethanol (mass %) | 0 |

To 0.5 mL of the self-emulsifiable composition thus obtained, a 10-fold volume of water, that is, 5 mL, was added, and thereby a nanoemulsion was produced. Next, immediately after preparation of the nanoemulsion, and after leaving the nanoemulsion to stand for 2 hours after preparation, the average particle size was measured. Measurement of the average particle size was carried out using a measuring apparatus that utilized a dynamic light scattering method (Coulter N4 Plus submicron particle size distribution analyzer, manufactured by Beckman Coulter, Inc.), and the average particle size was determined as a volume-reduced value. The results are presented in Table 3.

TABLE 3

| | Average particle size of nanoemulsion (nm) | |
| --- | --- | --- |
| Sparingly soluble substance (10 mg/g) | Upon 10-times dilution | Immediately after standing for 2 hours |
| None | 18 | 20 |
| Nifedipine | 17 | 17 |
| Furosemide | 28 | 27 |
| Acemetacin | 90 | 94 |
| Tacrolimus | 29 | 29 |

When an egg yolk-derived monoacyl phospholipid was used in combination with an egg yolk-derived diacyl phospholipid, a self-emulsifiable composition containing a sparingly soluble substance was obtained, without incorporating ethanol. Furthermore, all of the self-emulsifiable compositions containing a sparingly soluble substance thus obtained can produce nanoemulsions having an average particle size of 100 nm or less by a simple operation such as addition of water, and the nanoemulsions thus produced were stable without any change in the average particle size, even after standing for 2 hours.

Test Example 3: Preparation and Evaluation of Self-Emulsifiable Composition (2)

Self-emulsifiable compositions were obtained according to the compositions indicated in Table 4 by an operation similar to that of Test Example 1. To 0.5 mL of the self-emulsifiable composition thus obtained, a 10-fold volume of water, that is, 5 mL, was added, and thereby a nanoemulsion was produced. Measurement of the average particle size of the nanoemulsion was carried out using a measuring apparatus that utilized a dynamic light scattering method (Coulter N4 Plus submicron particle size distribution analyzer, manufactured by Beckman Coulter, Inc.), and the average particle size was determined as a volume-reduced value. The results are presented in Table 5 and FIG. 1.

TABLE 4

| | Monoacyl phospholipid | | Diacyl phospholipid | | Oils and fats | | Polyhydric alcohol | |
|---|---|---|---|---|---|---|---|---|
| | Type | Content (g) | Type | Content (g) | Type | Content (g) | Type | Content (g) |
| a | LPC1 | 1.0 | 98T | 1.0 | MCT | 0.5 | Glycerin | 2.0 |
| b | LPC1 | 1.0 | 100M | 1.0 | MCT | 0.5 | Glycerin | 4.0 |
| c | LPC1 | 1.0 | 100M | 1.0 | MCT | 0.5 | Glycerin | 8.0 |
| d | LPC1 | 1.0 | 100M | 1.0 | MCT | 0.5 | Glycerin | 16.0 |
| e | LPC1 | 1.0 | 100M | 1.0 | MCT | 2.0 | Glycerin | 6.0 |
| f | LPC1 | 2.0 | 98T | 2.0 | MCT | 0.5 | Glycerin | 1.0 |
| g | LPC1 | 2.0 | 98T | 2.0 | MCT | 0.5 | Glycerin | 2.0 |
| h | LPC1 | 2.0 | 98T | 2.0 | MCT | 0.5 | Glycerin | 3.0 |
| i | LPC1 | 2.0 | 98T | 2.0 | MCT | 0.5 | Glycerin | 4.0 |
| j | LPC1 | 2.0 | 98T | 2.0 | MCT | 1.0 | PG | 3.0 |
| k | LPC1 | 2.0 | 98T | 2.0 | MG_C10 | 2.0 | Glycerin | 8.0 |
| l | LPC1 | 2.0 | 98T | 2.0 | C8EE | 4.0 | Glycerin | 8.0 |
| m | LPC1 | 3.0 | 98T | 3.0 | C8EE | 4.0 | Glycerin | 1.0 |
| n | LPC1 | 3.0 | 98T | 3.0 | C8EE | 4.0 | Glycerin | 3.0 |
| o | LPC1 | 3.0 | 98T | 3.0 | C8EE | 4.0 | Glycerin | 5.0 |
| p | LPC1 | 3.5 | 98T | 3.5 | C8EE | 3.0 | Glycerin | 3.0 |
| q | LPC1 | 3.5 | 98T | 3.5 | C8EE | 3.0 | Glycerin | 5.0 |
| r | LPC1 | 2.0 | 100M | 2.0 | IPM | 2.0 | Glycerin | 15.0 |
| s | LPC1 | 2.0 | 100M | 2.0 | Soybean oil | 0.25 | Glycerin | 6.0 |
| t | LPC1 | 1.1 | 100M | 1.1 | MCT | 0.5 | Glycerin | 4.5 |
| | | | | | | | Sorbitol | 7.0 |
| u | LPC1 | 4.0 | 100M | 4.0 | MCT | 2.0 | Sorbitol | 30 |
| v | LPC1 | 4.5 | 98T | 1.5 | MCT | 0.25 | PG | 3.75 |
| w | LPC1 | 3.0 | 98T | 1.0 | EPAEE | 1.0 | PG | 2.3 |
| x | LPC1 | 3.0 | 98T | 1.0 | C18EE | 3.0 | PG | 3.0 |

The abbreviations in Table 4 represent the following.
LPC1: Egg yolk lysolecithin LPC-1 (lysophosphatidylcholine 90%) (manufactured by Kewpie Corporation)
100M: Egg yolk lecithin PL-100M (phosphatidylcholine 80%, phosphatidylethanolamine 20%) (manufactured by Kewpie Corporation)
98T: Purified egg yolk lecithin PC-98T (phosphatidylcholine 98%) (manufactured by Kewpie Corporation)
MCT: Medium-chain fatty acid triglycerides (manufactured by Kao Corporation)
MG_C10: Monocapric acid (manufactured by KANTO CHEMICAL CO., INC.)
C8EE: Caprylic acid ethyl ester (manufactured by KANTO CHEMICAL CO., INC.)
IPM: Isopropyl myristate (manufactured by KANTO CHEMICAL CO., INC.)
C18EE: Oleic acid ethyl ester (manufactured by Wako Pure Chemical Industries, Ltd.)
EPAEE: Eicosapentaenoic acid ethyl ester (manufactured by Kewpie Corporation)
PG: Propylene glycol (manufactured by ADEKA Corporation)
Sorbitol: 70% aqueous solution of sorbitol (manufactured by Kao Corporation)

TABLE 5

| | Content (mass %) of each component with respect to 100 mass % of total content of phospholipids, oils and fats, and polyhydric alcohol | | | Average particle size of nanoemulsion |
|---|---|---|---|---|
| | Total of phospholipids (x) | Oils and fats (y) | Polyhydric alcohol (z) | after addition of water (nm) |
| a | 44 | 11 | 44 | 26 |
| b | 31 | 8 | 62 | 24 |
| c | 19 | 5 | 76 | 28 |
| d | 11 | 3 | 86 | 20 |
| e | 20 | 20 | 60 | 570 |
| f | 73 | 9 | 18 | 328 |
| g | 62 | 8 | 31 | 232 |
| h | 53 | 7 | 40 | 187 |
| i | 47 | 6 | 47 | 91 |
| j | 50 | 13 | 38 | 15 |
| k | 28 | 15 | 57 | 236 |
| l | 25 | 25 | 50 | 184 |
| m | 55 | 36 | 9 | 374 |
| n | 46 | 31 | 23 | 232 |
| o | 40 | 27 | 33 | 234 |
| p | 54 | 23 | 23 | 276 |
| q | 47 | 20 | 33 | 234 |
| r | 19 | 10 | 71 | 15 |
| s | 40 | 2 | 58 | 143 |
| t | 15 | 4 | 81 | 12 |
| u | 20 | 5 | 75 | 230 |
| v | 60 | 3 | 37 | 28 |
| w | 55 | 14 | 32 | 28 |
| x | 40 | 30 | 30 | 62 |

Even in a case in which the types and contents of the monoacyl phospholipid, diacyl phospholipid, oils and fats, and polyhydric alcohol were changed, a self-emulsifiable composition was obtained without incorporating ethanol. All of the self-emulsifiable compositions thus obtained could produce nanoemulsions by a simple operation such as addition of water. In particular, when the total content of the monoacyl phospholipid and the diacyl phospholipid was designated as x % by mass, the content of the oils and fats was designated as y % by mass, and the content of the polyhydric alcohol was designated as z % by mass, with respect to 100% by mass of the total content of the monoacyl phospholipid, diacyl phospholipid, oils and fats, and polyhydric alcohol, in a case in which x, y, and z were within a region surrounded by a triangle having point A (x, y, z)=(0.1, 0.1, 99.8), point B (x, y, z)=(65.0, 0.1, 34.9), and point C (x, y, z)=(45.0, 40.0, 15.0) in the triangular diagram shown in FIG. 1 as apexes, a nanoemulsion having an average particle size of 250 nm or less could be produced. Furthermore, in a case in which x, y, and z were within a region surrounded by a triangle having point A' (x, y, z)=(0.1, 0.1, 99.8), point B' (x, y, z)=(50.0, 4.1, 45.9), and point C' (x, y, z)=(45.0, 20.0, 35.0) in the triangular diagram shown in FIG. 1 as apexes, a nanoemulsion having an average particle size of 100 nm or less could be produced efficiently.

Test Example 4: Preparation and Evaluation of
Self-Emulsifiable Composition Containing
Sparingly Soluble Drug (2)

As sparingly soluble substances, cyclosporine A (solubility: "almost not soluble"), tacrolimus (solubility: "almost not soluble"), and indomethacin (solubility: "almost not soluble"), all of which are sparingly soluble drugs, were used. First, a self-emulsifiable composition was obtained according to the composition indicated in Table 6 by an operation similar to that of Test Example 1. Next, 5 g of the self-emulsifiable composition thus obtained was added to a sparingly soluble substance, and about 10 mL of ethanol was further added thereto. This was warmed for 5 minutes in a warm bath at 60° C., and thereby the sparingly soluble substance was dissolved. Next, ethanol was distilled off using a rotary evaporator, and thereby a self-emulsifiable composition containing the sparingly soluble substance was obtained.

TABLE 6

| Blend | |
|---|---|
| Egg yolk-derived monoacyl phospholipid (g) | 37.5 |
| Egg yolk-derived diacyl phospholipid (g) | 12.5 |
| Polyhydric alcohol (propylene glycol) (g) | 47.5 |
| Oils and fats (medium-chain fatty acid triglycerides) (g) | 2.5 |
| Content of phospholipids (mass %) | 50 |
| Content of ethanol (mass %) | 0 |

To 0.5 mL of the self-emulsifiable composition thus obtained, a 10-fold volume of water, that is, 5 mL, was added, and thereby a nanoemulsion was produced. Next, the average particle size was measured immediately after preparation of the nanoemulsion. Measurement of the average particle size was carried out using a measuring apparatus that utilized a dynamic light scattering method (Coulter N4 Plus submicron particle size distribution analyzer, manufactured by Beckman Coulter, Inc.), and the average particle size was determined as a volume-reduced value. The results are presented in Table 7.

TABLE 7

| Sparingly soluble substance (concentration) | Average particle size of nanoemulsion (nm) Upon 10-times dilution |
|---|---|
| None | 14 |
| Cyclosporine A (100 mg/g) | 26 |
| Tacrolimus (100 mg/g) | 25 |
| Indomethacin (75 mg/g) | 28 |

Similar to Test Example 2, when an egg yolk-derived monoacyl phospholipid was used in combination with an egg yolk-derived diacyl phospholipid, a self-emulsifiable composition containing a sparingly soluble substance was obtained without incorporating ethanol. Furthermore, all of the self-emulsifiable compositions containing a sparingly soluble substance thus obtained could produce nanoemulsions having an average particle size of 100 nm or less, by a simple operation such as addition of water.

The invention claimed is:

1. A self-emulsifiable composition, consisting of:
a monoacyl phospholipid, a diacyl phospholipid, oils and fats, a polyhydric alcohol, and optionally a sparingly soluble substance, wherein:
the content ratio between the monoacyl phospholipid and the diacyl phospholipid is in the range of monoacyl phospholipid:diacyl phospholipid=1:9 to 9:1 as a mass ratio,
when the total content of the monoacyl phospholipid and the diacyl phospholipid is designated as x % by mass, the content of the oils and fats is designated as y % by mass, and the content of the polyhydric alcohol is designated as z % by mass, with respect to 100% by mass of the total content of the monoacyl phospholipid, the diacyl phospholipid, the oils and fats, and the polyhydric alcohol, x, y, and z are within a region surrounded by a triangle having the following points A, B, and C in a triangular diagram (x, y, z) as apexes:
A: (x, y, z)=(0.1, 0.1, 99.8)
B: (x, y, z)=(65.0, 0.1, 34.9)
C: (x, y, z)=(45.0, 40.0, 15.0).

2. The self-emulsifiable composition according to claim 1, wherein the sparingly soluble substance is present.

3. The self-emulsifiable composition according to claim 1, wherein an average particle size obtainable when the self-emulsifiable composition is mixed with a 10-fold volume of water is 250 nm or less.

4. The self-emulsifiable composition according to claim 1, wherein the total content of the monoacyl phospholipid and the diacyl phospholipid is from 0.1% by mass to 70% by mass.

5. The self-emulsifiable composition according to claim 1, wherein the oils and fats include medium-chain fatty acids.

6. The self-emulsifiable composition according to claim 1, wherein the content of the oils and fats satisfies the requirement of being from 0.1% by mass to 35% by mass based on the total amount of the composition, or being from 0.1 part by mass to 70 parts by mass with respect to 100 parts by mass of the total content of the monoacyl phospholipid and the diacyl phospholipid.

7. The self-emulsifiable composition according to claim 1, wherein the content of the polyhydric alcohol is from 20% by mass to 99% by mass based on the total amount of the composition.

8. The self-emulsifiable composition according to claim 1, wherein x, y, and z are within a region surrounded by a triangle having the following points A', B', and C' in a triangular diagram (x, y, z) as apexes:
A': (x, y, z)=(0.1, 0.1, 99.8)
B': (x, y, z)=(50.0, 4.1, 45.9)
C': (x, y, z)=(45.0, 20.0, 35.0).

9. A self-emulsifiable composition, consisting of:
a monoacyl phospholipid, a diacyl phospholipid, oils and fats, and a polyhydric alcohol, wherein:
the content ratio between the monoacyl phospholipid and the diacyl phospholipid is in the range of monoacyl phospholipid:diacyl phospholipid=1:9 to 9:1 as a mass ratio,
when the total content of the monoacyl phospholipid and the diacyl phospholipid is designated as x % by mass, the content of the oils and fats is designated as y % by mass, and the content of the polyhydric alcohol is designated as z % by mass, with respect to 100% by mass of the total content of the monoacyl phospholipid, the diacyl phospholipid, the oils and fats, and the polyhydric alcohol, x, y, and z are within a region surrounded by a triangle having the following points A, B, and C in a triangular diagram (x, y, z) as apexes:
A: (x, y, z)=(0.1, 0.1, 99.8)
B: (x, y, z)=(65.0, 0.1, 34.9)
C: (x, y, z)=(45.0, 40.0, 15.0).

* * * * *